US010512433B2

(12) United States Patent
Ikemoto et al.

(10) Patent No.: US 10,512,433 B2
(45) Date of Patent: Dec. 24, 2019

(54) CORRECTION DATA GENERATION METHOD AND CORRECTION DATA GENERATION APPARATUS

(71) Applicant: HOYA CORPORATION, Tokyo (JP)

(72) Inventors: Yousuke Ikemoto, Tokyo (JP); Tadashi Minakuchi, Saitama (JP); Atsushi Komoro, Ibaraki (JP); Toshio Tachibana, Ibaraki (JP); Yoichi Hitokata, Saitama (JP); Noriko Ota, Tokyo (JP)

(73) Assignee: HOYA CORPORATION, Tokyo (JP)

( * ) Notice: Subject to any disclaimer, the term of this patent is extended or adjusted under 35 U.S.C. 154(b) by 164 days.

(21) Appl. No.: 15/554,085

(22) PCT Filed: Feb. 3, 2017

(86) PCT No.: PCT/JP2017/003945
§ 371 (c)(1),
(2) Date: Aug. 28, 2017

(87) PCT Pub. No.: WO2017/150071
PCT Pub. Date: Sep. 8, 2017

(65) Prior Publication Data
US 2018/0168512 A1    Jun. 21, 2018

(30) Foreign Application Priority Data

Mar. 3, 2016   (JP) .................................. 2016-040599

(51) Int. Cl.
*A61B 5/00*      (2006.01)
*A61B 1/00*      (2006.01)
(Continued)

(52) U.S. Cl.
CPC ........ *A61B 5/7203* (2013.01); *A61B 1/00055* (2013.01); *A61B 5/1032* (2013.01);
(Continued)

(58) Field of Classification Search
CPC ... A61B 34/20; A61B 1/00009; A61B 5/1032; A61B 1/045; A61B 1/0638; A61B 5/061;
(Continued)

(56) References Cited

U.S. PATENT DOCUMENTS

2003/0071895 A1    4/2003   Higuchi et al.
2003/0103212 A1*   6/2003   Westphal ............... A61B 3/102
                                                           356/479
(Continued)

FOREIGN PATENT DOCUMENTS

| JP | 63-79631  | 4/1988 |
| JP | 63-173182 | 7/1988 |

(Continued)

OTHER PUBLICATIONS

International Search Report issued in International Patent Application No. PCT/JP2017/003945, dated Apr. 25, 2017, along with English-langauge translation.

(Continued)

*Primary Examiner* — Aklilu K Woldemariam
(74) *Attorney, Agent, or Firm* — Greenblum & Bernstein, P.L.C.

(57) ABSTRACT

Provided is a correction data generation method that includes acquiring captured image data by imaging an indicator that is related to a predetermined illness; plotting a real imaging data point that corresponds to the acquired captured image data in a predetermined color space that is associated with the predetermined illness in accordance with a color component of the data point; calculating a correction value for correcting the values of pixels that make up a captured image captured by an electronic endoscope based on the distance between the data point and a predetermined target point in the predetermined color space; and storing the calculated correction value.

14 Claims, 6 Drawing Sheets

(51) Int. Cl.
*A61B 5/103* (2006.01)
*A61B 5/145* (2006.01)
*A61B 5/1459* (2006.01)
*G06T 3/40* (2006.01)
*H04N 1/60* (2006.01)

(52) U.S. Cl.
CPC ........ *A61B 5/1459* (2013.01); *A61B 5/14546* (2013.01); *A61B 5/4842* (2013.01); *G06T 3/4015* (2013.01); *H04N 1/6005* (2013.01)

(58) Field of Classification Search
CPC ..... A61B 5/441; A61B 5/445; A61B 1/00052; A61B 1/05; A61B 1/0669; A61B 1/07; A61B 1/04; A61B 1/00048; A61B 1/00055; A61B 5/14546; A61B 5/1459; A61B 5/4842; A61B 5/7203; A61B 34/30; A61B 5/0064; A61B 1/317; A61B 1/041; A61B 1/00; G06T 2207/10068; G06T 7/0012; G06T 2207/10024; G06T 2207/20172; G06T 2207/30028; G06T 2207/30096; G06T 5/007; G06T 7/0014; G06T 19/20; G06T 2207/30004; G06T 2207/10016; G06T 2207/10004; G06T 3/4015; G06T 7/90; G06T 7/215; G06G 3/3208; H04N 1/6083; H04N 7/183; H04N 9/73; H04N 9/735; H04N 1/401; H04N 1/6033; H04N 5/3572; H04N 1/6005; H04N 2005/2255; H04N 7/181; H04N 5/217; G06F 19/321; G01N 21/314; G01N 2021/1787; G06K 2209/05; G06K 9/4652; G06K 9/6217; G06K 9/6214; G02B 21/367
USPC ...... 382/128, 133, 134, 167; 348/61, 65, 79, 348/370
See application file for complete search history.

(56) References Cited

U.S. PATENT DOCUMENTS

| | | | |
|---|---|---|---|
| 2003/0113014 A1 | 6/2003 | Katoh | |
| 2005/0068503 A1* | 3/2005 | Imade | G03B 21/16 353/31 |
| 2005/0190994 A1* | 9/2005 | Yamanaka | G06T 1/00 382/305 |
| 2008/0240558 A1* | 10/2008 | Li | H04N 1/00045 382/167 |
| 2009/0208071 A1* | 8/2009 | Nishimura | A61B 1/041 382/128 |
| 2010/0074508 A1 | 3/2010 | Shinoda et al. | |
| 2010/0278404 A1* | 11/2010 | Takei | A61B 1/0638 382/128 |
| 2011/0069876 A1* | 3/2011 | Kanda | A61B 1/00052 382/134 |
| 2013/0028485 A1* | 1/2013 | Kitamura | G06T 7/0012 382/106 |
| 2013/0109915 A1* | 5/2013 | Krupnik | G06T 3/4038 600/109 |
| 2013/0322537 A1* | 12/2013 | Rossato | H04N 19/63 375/240.16 |
| 2014/0320620 A1 | 10/2014 | Ikemoto et al. | |
| 2015/0097994 A1* | 4/2015 | Yokoyama | H04N 5/3572 348/242 |
| 2015/0193929 A1 | 7/2015 | Ikemoto | |
| 2015/0208958 A1* | 7/2015 | Kaku | A61B 5/1459 600/339 |

FOREIGN PATENT DOCUMENTS

| | | |
|---|---|---|
| JP | 1-101960 | 4/1989 |
| JP | 6-46428 | 2/1994 |
| JP | 8-23449 | 1/1996 |
| JP | 2000-41942 | 2/2000 |
| JP | 2002-142231 | 5/2002 |
| JP | 2003-93337 | 4/2003 |
| JP | 2010-79522 | 4/2010 |
| JP | 2013-240701 | 12/2013 |
| JP | 2014-18332 | 2/2014 |
| JP | 2014-213094 | 11/2014 |
| JP | 2016-15995 | 2/2016 |
| WO | 2012/147505 | 11/2012 |

OTHER PUBLICATIONS

Japanese Office Action for JP App. No. 2017-543849 dated Jul. 9, 2018.
Office Action issued in Japan Counterpart Patent Appl. No. 2018-201962, dated Aug. 8, 2019.

\* cited by examiner

CORRECTION DATA GENERATION METHOD AND CORRECTION DATA GENERATION APPARATUS

TECHNICAL FIELD

The present invention relates to a correction data generation method and a correction data generation apparatus.

BACKGROUND ART

A lesion site generally has a different color from normal mucosal tissue. In recent years, improvements in the performance of color endoscope apparatuses have made it possible for an operator to identify and diagnose a lesion site whose color is slightly different from normal tissue. However, an operator needs extensive training under the guidance of an expert in order to be able to accurately distinguish a lesion site from normal tissue based on a slight color difference in an image captured by an electronic endoscope and then make a diagnosis. Also, even an experienced operator may not be able to easily identify and diagnose a lesion site based on a slight color difference, and this requires careful work.

In view of this, JP 2014-18332A (referred to hereinafter as "Patent Document 1") is one example of a document that describes a device for scoring a lesion site that appears in a captured image in order to facilitate the diagnosis of a lesion site by an operator. Specifically, with the device described in Patent Document 1, the pixels that constitute an image captured by an electronic endoscope are subjected to tone enhancement processing for applying non-linear gain to the pixel values, the dynamic range is widened in the vicinity of the boundary of a region of pixel values that are to be subjected to lesion site determination, the tone-enhanced pixel data in an RGB space, which is defined by the three primary colors RGB, is converted to a predetermined color space such as the HIS color space or the HSV color space in order to acquire hue and saturation data, pixels are determined to be or not be lesion site pixels based on the acquired hue and saturation data, and then an evaluation value (lesion index) is calculated based on the number of pixels determined to be lesion site pixels.

SUMMARY OF INVENTION

In pixel data acquired by an electronic endoscope, R/G/B values do not take the same values for a white subject in the pixel data as-is. In view of this, the pixel data is subjected to white balance adjustment. In the apparatus illustrated in Patent Document 1, a lesion index is calculated based on color data acquired from a captured image, and therefore it is thought that an improvement in the color reproduction of a captured image through white balance adjustment is accompanied by an improvement in the calculation precision of the lesion index.

However, when the same lesion site is imaged by different electronic endoscope systems, there are cases where large variations occur in the score value of the lesion index or the like even if the lesion site visually appears to be the same. In view of this, through in-depth diligent examination, the inventors of the present invention found that mainly due to individual differences between the optical components (optical performance) of electronic endoscopes, error (variation) that could not be completely removed in white balance adjustment remains in color data used in score calculation, and this error is a cause of degradation in score calculation precision.

The present invention was achieved in light of the foregoing situation, and an object of the present invention is to provide a correction data generation method and a correction data generation apparatus for suppressing variation in score values when imaging the same lesion site with different electronic endoscope systems.

A correction data generation method according to a first aspect of the present invention is a correction data generation method executed by a computer, the method including: an acquiring step of acquiring captured image data by imaging an indicator that is related to a predetermined illness; a plotting step of plotting a real imaging data point that corresponds to the acquired captured image data in a predetermined color space that is associated with the predetermined illness in accordance with a color component of the data point; a calculating step of calculating a correction value for correcting values of pixels that make up a captured image captured by an electronic endoscope based on a distance between the data point and a predetermined target point in the predetermined color space; and a storing step of storing the calculated correction value.

Also, in the correction data generation method according to the first aspect of the present invention, in the acquiring step, first captured image data may be acquired by imaging a first indicator of a first color that is a color of biological tissue when a symptom level is a predetermined first level with respect to the predetermined illness, and second captured image data may be acquired by imaging a second indicator of a second color that is a color of biological tissue when a symptom level is a predetermined second level with respect to the illness, in the plotting step, first and second data points that correspond to the acquired first and second captured image data may be plotted in the predetermined color space in accordance with color components of the first and second data points, and in the calculating step, the correction value may be calculated based on a distance between the first data point and the predetermined first target point in the predetermined color space and a distance between the second data point and the predetermined second target point in the predetermined color space.

Also, the correction data generation method according to the first aspect of the present invention may further include: a step of accepting an operation designating a symptom level from a user; and a step of informing the user of an indicator that corresponds to the accepted symptom level.

Also, in the correction data generation method according to the first aspect of the present invention, in the calculating step, a matrix coefficient that obtains a lowest sum value of the distance between the first data point and the first target point and the distance between the second data point and the second target point may be calculated as the correction value.

Also, in the correction data generation method according to the first aspect of the present invention, the color space is a two-dimensional color space that includes an R component axis and a G component axis that is orthogonal to the R component axis, for example.

Also, in the correction data generation method according to the first aspect of the present invention, the first color is a color of biological tissue when the symptom level is highest with respect to the illness, for example. In this case, the first target point is a point located on an axis highly correlated with hemoglobin pigment in the predetermined color space.

Also, in the correction data generation method according to the first aspect of the present invention, the second color is a color of biological tissue that is healthy with respect to the illness, for example. In this case, the second target point is a point located on an axis highly correlated with a hue of a mucous membrane in a body cavity in the predetermined color space.

Also, a correction data generation apparatus according to a second aspect of the present invention includes: an acquiring means for acquiring captured image data by imaging an indicator that is related to a predetermined illness; a plotting means for plotting a real imaging data point that corresponds to the acquired captured image data in a predetermined color space that is associated with the predetermined illness in accordance with a color component of the data point; a calculating means for calculating a correction value for correcting values of pixels that make up a captured image captured by an electronic endoscope based on a distance between the data point and a predetermined target point in the predetermined color space; and a storing means for storing the calculated correction value.

According to aspects of the present invention, it is possible to provide a correction data generation method and a correction data generation apparatus for suppressing variation in score values when imaging the same lesion site with different electronic endoscope systems.

DESCRIPTION OF EMBODIMENTS

Hereinafter, embodiments of the present invention will be described with reference to the drawings. Note that an electronic endoscope system (computer) is taken as an example of an embodiment of the present invention in the following description.

Configuration of Electronic Endoscope System 1

Figure 1:
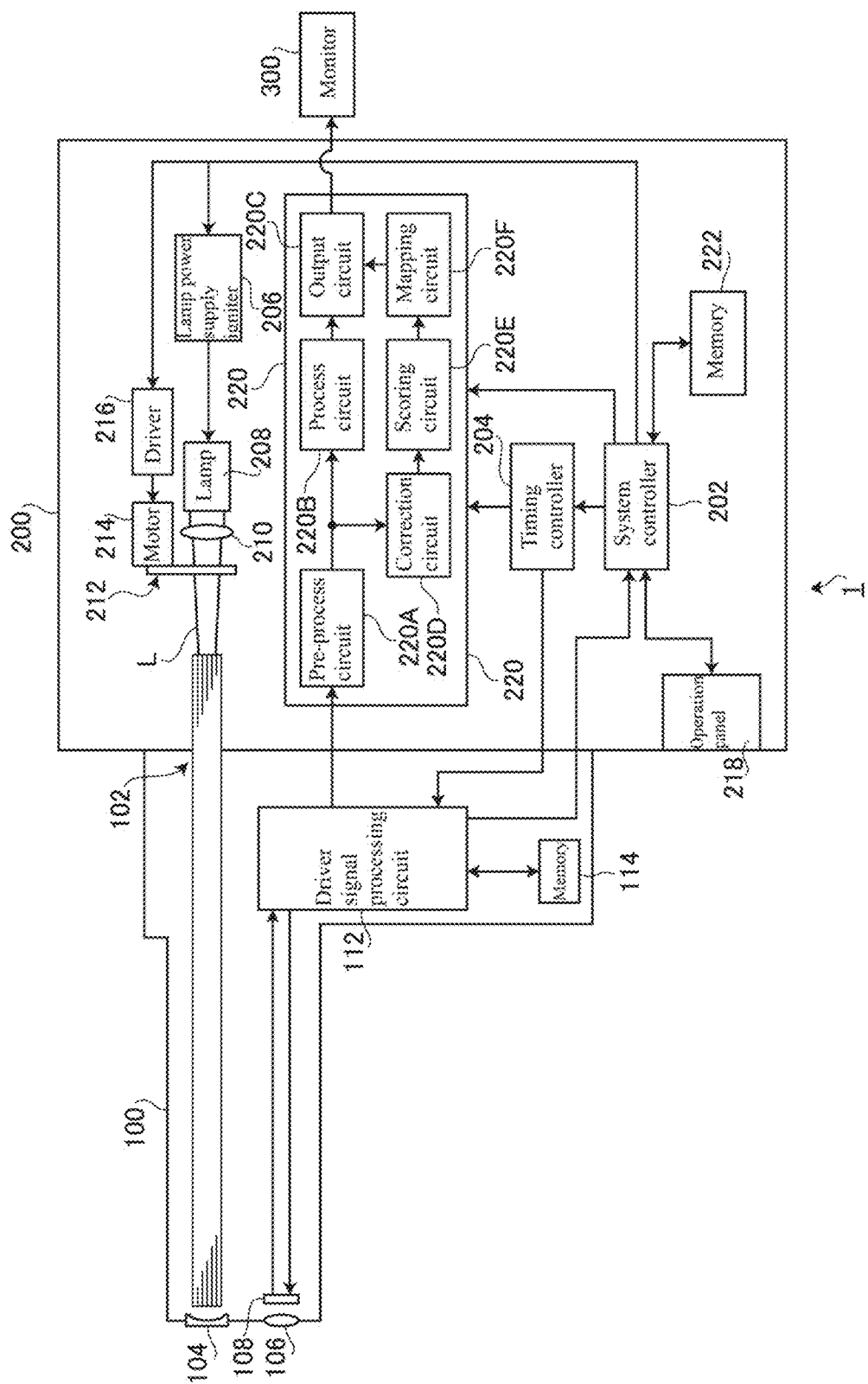
FIG. 1 is a block diagram showing a configuration of an electronic endoscope system according to an embodiment of the present invention.

FIG. 1 is a block diagram showing the configuration of an electronic endoscope system 1 according to an embodiment of the present invention. As shown in FIG. 1, the electronic endoscope system 1 is a system specialized for medical use, and includes an electronic endoscope 100, a processor 200, and a monitor 300.

The processor 200 includes a system controller 202 and a timing controller 204. The system controller 202 executes various programs stored in a memory 222 and performs overall control of the electronic endoscope system 1. Also, the system controller 202 is connected to an operation panel 218. The system controller 202 changes operations of the electronic endoscope system 1 and parameters for various operation in accordance with instructions from an operator that are input using the operation panel 218. One example of an instruction input by an operator is an instruction for switching the operating mode of the electronic endoscope system 1. In the present embodiment, the operating modes include a normal mode, a special mode, and a calibration mode. The timing controller 204 outputs a clock pulse, which is for adjustment of the timing of the operations of portions, to circuits in the electronic endoscope system 1.

The lamp 208 is activated by a lamp power supply igniter 206, and thereafter emits white light L. The lamp 208 is a high-intensity lamp such as a xenon lamp, a halogen lamp, a mercury lamp, or a metal halide lamp. The white light L emitted by the lamp 208 is condensed by a condensing lens 210 and limited to an appropriate light amount via a diaphragm 212. Note that the lamp 208 may be replaced with a semiconductor light emitting element such as an LD (Laser Diode) or an LED (Light Emitting Diode). A semiconductor light emitting element has features such as having a lower power consumption and smaller heat emission amount than other light sources, and therefore has an advantage of making it possible to acquire bright images while also suppressing power consumption and the heat emission amount. The ability to acquire bright images leads to an improvement in the precision of a later-described inflammation evaluation value. The semiconductor light emitting element is not limited to being provided in the processor 200, and may be provided in the electronic endoscope 100. For example, the semiconductor light emitting element may be provided in the distal end portion of the electronic endoscope 100.

A motor 214 is mechanically coupled to the diaphragm 212 via transmission mechanisms such as an arm and a gear, which are not shown. The motor 214 is a DC motor for example, and is driven under drive control of a driver 216. The diaphragm 212 is operated by the motor 214, and the opening degree is changed in order to set the images displayed on the display screen of a monitor 300 to an appropriate brightness. The light amount of the white light L emitted by the lamp 208 is limited according to the opening degree of the diaphragm 212. The appropriate image brightness reference is set and changed according to an intensity adjustment operation performed on the operation panel 218 by the operator. Note that the light control circuit for performing intensity adjustment by controlling the driver 216 is a known circuit and will not be described in this specification.

The white light L that passes through the diaphragm 212 is condensed on the entrance end face of an LCB (Light Carrying Bundle) 102 and enters the LCB 102. The white light L that entered the LCB 102 through the entrance end face propagates inside the LCB 102.

After propagating inside the LCB 102, the white light L exits through an exit end face of the LCB 102 arranged at the leading end of the electronic endoscope 100, passes through a light distribution lens 104, and illuminates biological tissue. Returning light from the biological tissue illuminated by the white light L passes through an objective lens 106 and forms an optical image on the light receiving surface of a solid-state image sensor 108.

The solid-state image sensor 108 is a single-plate color CCD (Charge Coupled Device) image sensor that has a complimentary color checkered filter. The solid-state image sensor 108 accumulates charge according to the light quantity of an optical image formed on pixels on the light receiving surface, generates yellow Ye, cyan Cy, green G, and magenta Mg pixel data, and outputs the pixel data. Note that the solid-state image sensor 108 is not limited to being a CCD image sensor, and may be replaced with a CMOS (Complementary Metal Oxide Semiconductor) image sensor or another type of imaging apparatus. The solid-state image sensor 108 may be an element that includes a primary color filter (Bayer arrangement filter).

A driver signal processing circuit 112 is provided in the connection portion of the electronic endoscope 100. Pixel data from pixels that captured biological tissue illuminated by white light L are input by the solid-state image sensor 108 to the driver signal processing circuit 112 at a frame cycle. The pixel data input from the solid-state image sensor 108 is output by the driver signal processing circuit 112 to a signal processing circuit 220 of the processor 200. Note that the terms "frame" and "field" may be switched in the following description. In the present embodiment, the frame cycle and the field cycle are respectively 1/30 seconds and 1/60 seconds.

The driver signal processing circuit 112 also accesses a memory 114 and reads out unique information regarding the electronic endoscope 100. The unique information regarding the electronic endoscope 100 recorded in the memory 114 includes, for example, the pixel count, sensitivity, operable frame rate, and model number of the solid-state image sensor 108. The unique information read out from the memory 114 is output by the driver signal processing circuit 112 to a system controller 202.

The system controller 202 generates control signals by performing various computation based on the unique information regarding the electronic endoscope 100. The system controller 202 uses the generated control signals to control the operations of and the timing of various circuits in the processor 200 so as to perform processing suited to the electronic endoscope that is connected to the processor 200.

A timing controller 204 supplies a clock pulse to the driver signal processing circuit 112 in accordance with timing control performed by the system controller 202. In accordance with the clock pulse supplied from the timing controller 204, the driver signal processing circuit 112 controls the driving of the solid-state image sensor 108 according to a timing synchronized with the frame rate of the images processed by the processor 200.

Operations in Normal Mode

The following describes signal processing operations in the processor 200 in the normal mode.

The signal processing circuit 220 included in the processor 200 has a pre-process circuit 220A, a process circuit 220B, an output circuit 220C, a correction circuit 220D, a scoring circuit 220E, and a mapping circuit 220F.

The pre-process circuit 220A performs demosaic processing on RAW pixel data received from the driver signal processing circuit 112 at the frame cycle, performs conversion into RGB pixel data, performs color matrix processing, white balance adjustment, hue gain adjustment, and the like, and outputs the resulting pixel data to the process circuit 220B.

The process circuit 220B performs enhance processing, gamma correction, and the like on pixel data received from the pre-process circuit 220A, generates normal color image data, and outputs the image data to the output circuit 220C.

The output circuit 220C performs processing such as Y/C separation and color difference correction on the color image data received from the process circuit 220B, and performs conversion into a predetermined video format signal. The converted video format signal is output to the monitor 300. Accordingly, normal color images of the biological tissue are displayed on the display screen of the monitor 300.

Operations in Special Mode

Figure 2:
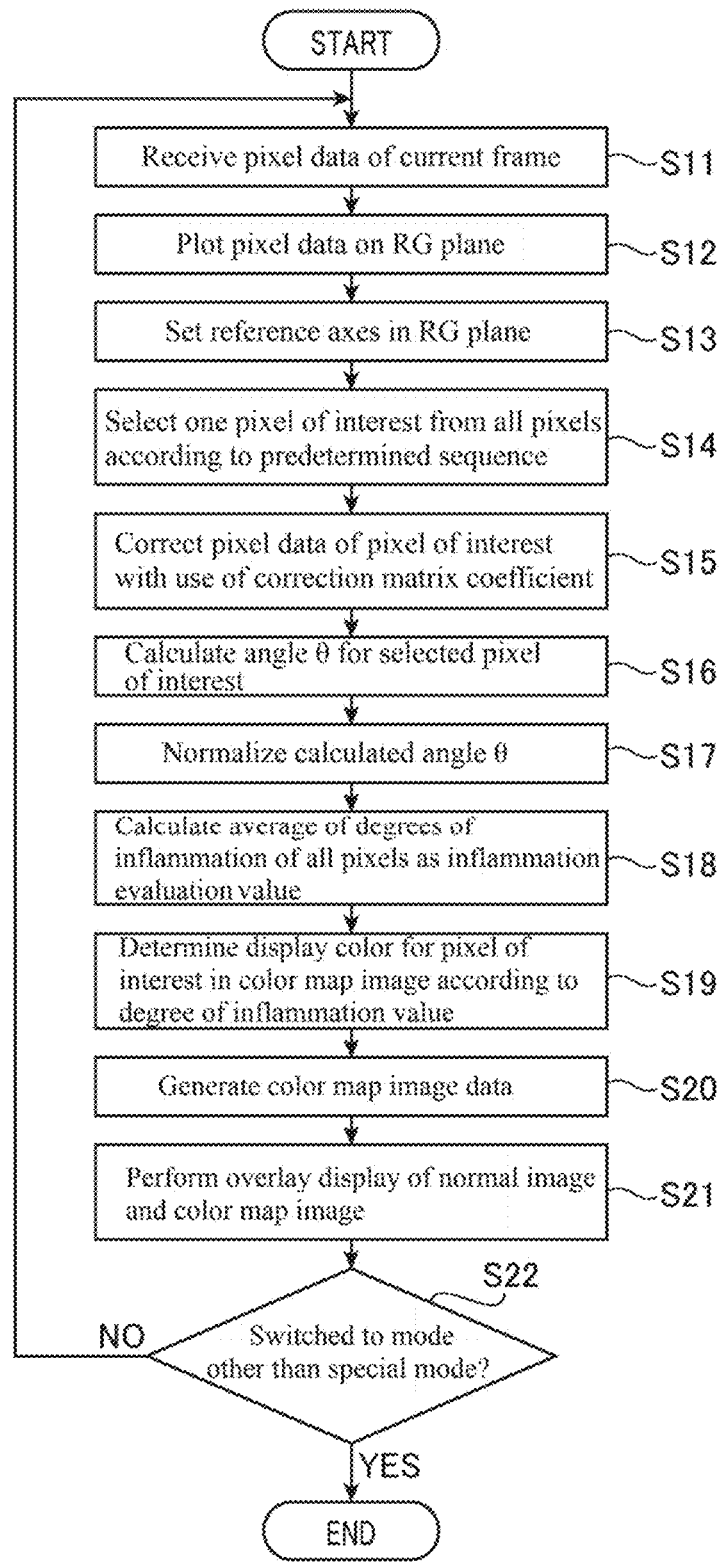
FIG. 2 is a diagram showing a flowchart of special image generation processing executed in a special mode according to an embodiment of the present invention.

Next, signal processing operations in the processor 200 in the special mode will be described. FIG. 2 shows a flowchart of special image generation processing executed in the special mode. The special image generation processing in FIG. 2 is started at the time when the operating mode of the electronic endoscope system 1 is switched to the special mode.

S11 in FIG. 2 (Input of Pixel Data of Current Frame)

In this processing step S11, pixel data for each pixel of the current frame is input to the pre-process circuit 220A. The pixel data for each pixel is subjected to signal processing by the pre-process circuit 220A and then input to the process circuit 220B and the correction circuit 220D.

S12 in FIG. 2 (Plotting on RG Plane)

Figure 3:
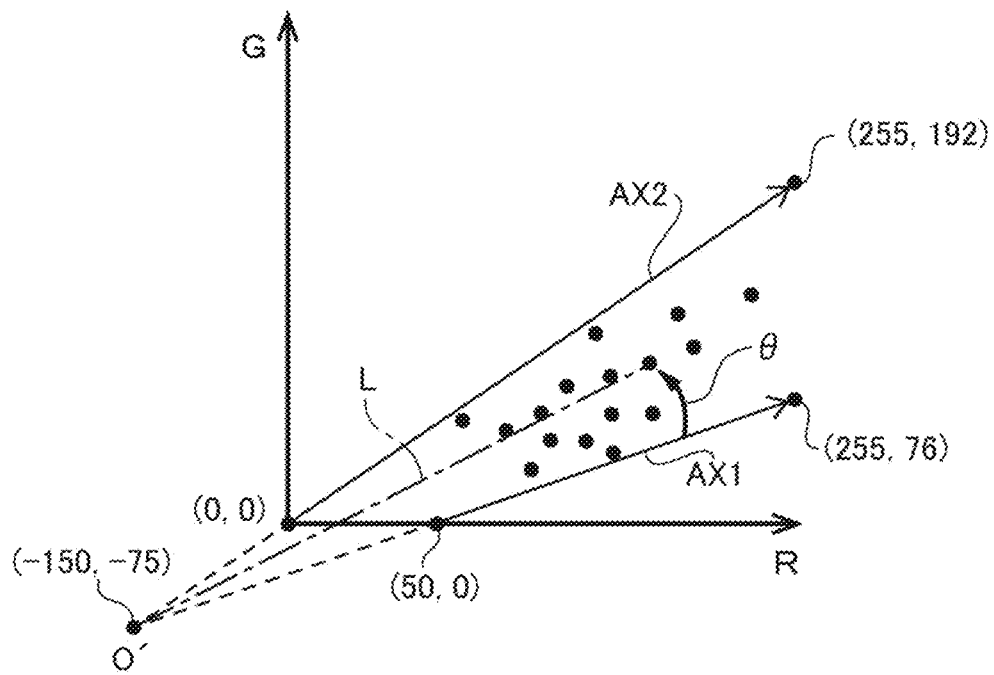
FIG. 3 is a diagram showing an RG plane on which pixel correspondence points are plotted in an embodiment of the present invention.

FIG. 3 is a diagram for conceptually illustrating operations of the correction circuit 220D, and shows an RG plane (two-dimensional color space) defined by an R axis and a G axis that are orthogonal to each other. Note that the R axis is the axis for the R component (R pixel values), and the G axis is the axis for the G component (G pixel values).

In this processing step S12, pixel data for each pixel in the RGB space defined by the three primary colors RGB (three-dimensional pixel data made up of three types of color components) is converted (orthographic projective transformation) into RG pixel data (two-dimensional pixel data made up of two types of color components). As conceptually shown in FIG. 3, the pixel data for each pixel in the RGB color space is plotted on the RG plane according to the R and G pixel values. Hereinafter for the sake of convenience in the description, the points corresponding to the pixel data plotted on the RG plane will be referred to as "pixel correspondence points". Note that for the sake of clarity in FIG. 3, pixel correspondence points are shown for only some pixels rather than for all of the pixels.

In this way, in this processing step S12, pixel data in the RGB space (three-dimensional data) is orthographically projected onto the RG plane, and the pixel correspondence points (two-dimensional data) are the feet of vertical lines dropped onto the RG plane from the points in the RGB space that correspond to the pixel data.

S13 in FIG. 2 (Setting of Reference Axis)

Figure 4:
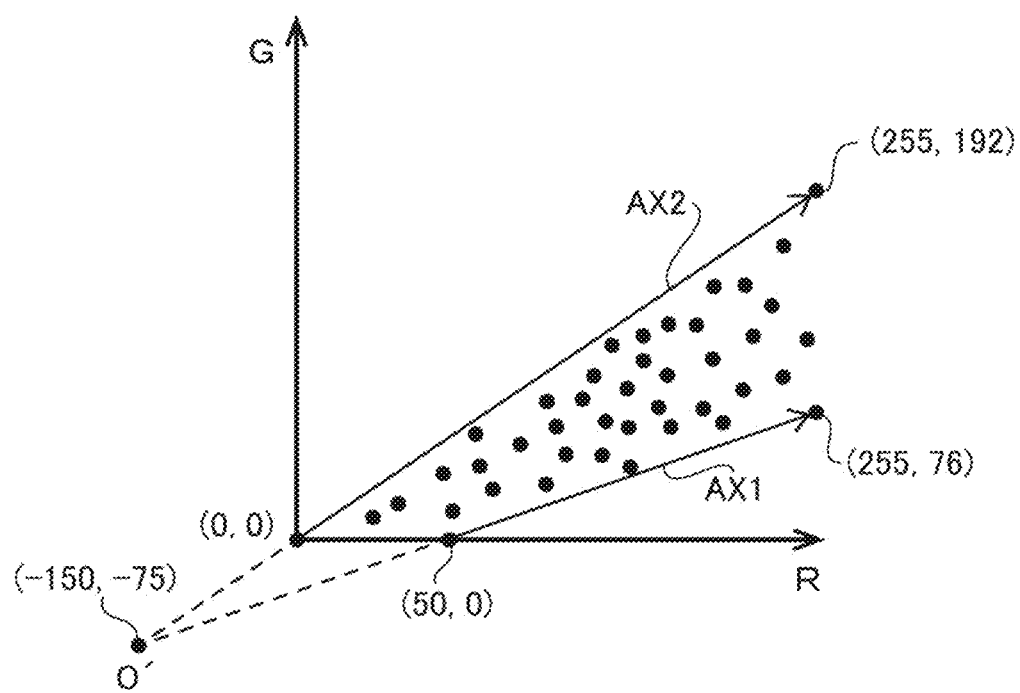
FIG. 4 is a diagram illustrating reference axes set in the RG plane.

In this processing step S13, a reference axis necessary for calculating the degree of inflammation of a predetermined illness such as gastritis is set in the RG plane by the correction circuit 220D. FIG. 4 shows a diagram for assisting the description of the reference axis.

Due to influences such as hemoglobin pigment, the R component is dominant over the other components (G component and B component) in the body cavity of the patient that is to be imaged, and the more intense the inflammation is, the redness (R component) typically increases relative to the other hues (G component and B component). However, in images captured inside a body cavity, the hue varies according to imaging conditions that influence brightness (e.g., degree of illumination with white light L). For example, shaded portions not reached by the white light L appear black (achromatic, with R, G, and B values at or near zero, for example), and portions where the white light L strikes intensely and is specularly reflected appear white (achromatic, with R, G, and B values at or near 255). In other words, even when the same inflamed abnormal site is imaged, the pixel value in the image of the abnormal site will be higher the more intensely the white light L strikes it. For this reason, depending on the degree of illumination with the white light L, the pixel value may take a value that has no correlation with the degree of inflammation.

Generally, normal sites inside a body cavity that are not inflamed are sufficiently covered by a mucous membrane. In contrast, abnormal sites inside a body cavity that are inflamed are not sufficiently covered by a mucous membrane. The mucous membrane is thinner the greater the degree of inflammation is at an abnormal site such as a lesion site. A mucous membrane is basically white in color, but has a slightly yellowish hue, and the hue (yellow hue) that appears in an image varies according to the darkness/lightness (membrane thickness). Accordingly, the darkness/lightness of the mucous membrane is also thought to be an indicator for evaluating the degree of inflammation.

In view of this, in this processing step S13, as shown in FIG. 4, a straight line that passes through (50,0) and (255,76) in the RG plane is set as one reference axis, and a straight line that passes through (0,0) and (255,192) is set as one reference axis. For the sake of convenience in the description, the former reference axis will be called the "hemoglobin variation axis AX1", and the latter reference axis will be called the "mucous membrane variation axis AX2".

The plot shown in FIG. 4 is the result of the inventor of the present invention analyzing a large number of sample images of body cavities. The sample images used in the analysis included examples of images of various stages of inflammation, including examples of images of inflammation of the highest symptom level (examples of images of inflammation of the most severe level) and examples of images of inflammation of the lowest symptom level (examples of images deemed to be substantially normal sites). Note that for the sake of clarity in the diagram, only a portion of the points obtained as analysis results is shown in the example in FIG. 4. The actual points obtained as analysis results are much higher in number than the number of points shown in FIG. 4.

As described above, the higher the degree of inflammation at an abnormal site is, the more intense the R component is relative to the other components (G component and B component). For this reason, an axis on the boundary line that separates regions where points are distributed and are not distributed, and that is closer to the R axis than the G axis, which is the boundary line that passes through (50,0) and (255,76) in the example in FIG. 4, is set as the axis having a high correlation with a lesion site that has the highest symptom level (an inflamed (abnormal) site with the highest symptom level). This axis is the hemoglobin variation axis AX1. Points that correspond to inflamed sites that have the highest symptom level and were imaged under various imaging conditions (e.g., degree of illumination with the white light L) are located on the hemoglobin variation axis AX1.

On the other hand, the closer a site approximates a normal site, the more intense the G component (or the B component) is relative to the R component. For this reason, an axis on the boundary line that separates regions where points are distributed and are not distributed, and that is closer to the G axis than the R axis, which is the boundary line that passes through (0,0) and (255,192) in the example in FIG. 4, is set as the axis having a high correlation with a lesion site with the lowest symptom level (an inflamed (abnormal) site with the lowest symptom level, which is deemed to be a substantially normal (healthy) site). This axis is the mucous membrane variation axis AX2. Points that correspond to inflamed sites that have the lowest symptom level (deemed to be substantially normal sites) and were imaged under various imaging conditions (e.g., degree of illumination with the white light L) are located on the mucous membrane variation axis AX2.

To give a further description, an inflamed site with the highest symptom level is accompanied by bleeding. On the other hand, an inflamed site with the lowest symptom level is a substantially normal site, and therefore is covered by a sufficient mucous membrane. For this reason, it can be understood that the points in the RG plane shown in FIG. 4 are distributed in the region sandwiched between the axis that has the highest correlation with blood (hemoglobin pigment) and the axis that has the highest correlation with the hue of the mucous membrane. For this reason, out of the boundary lines that separate regions where points are distributed and are not distributed, the boundary line closer to the R axis (higher R component) corresponds to the axis that indicates an inflamed site with the highest symptom level (hemoglobin variation axis AX1), and the boundary line closer to the G axis (higher G component) corresponds to the axis that indicates an inflamed site with the lowest symptom level (mucous membrane variation axis AX2).

S14 in FIG. 2 (Selection of Pixel of Interest)

In this processing step S14, one pixel of interest is selected by the correction circuit 220D from among all of the pixels in accordance with a predetermined sequence.

S15 in FIG. 2 (Correction of Pixel Data)

The correction circuit 220D stores a correction matrix coefficient that was calculated during the later-described calibration mode. In this processing step S15, in order to suppress variation in score values when the same lesion site is imaged with different electronic endoscope system (in other words, individual differences between electronic endoscopes), the pixel data (R,G) of the pixel of interest that was selected in processing step S14 (selection of pixel of interest) is corrected by the correction circuit 220D with use of the correction matrix coefficient. Note that the correction matrix coefficient will be described in detail in the later section "Operations in calibration mode".

Example of Correction Matrix $$\begin{pmatrix} R_{new} \\ G_{new} \end{pmatrix} = \begin{pmatrix} M_{11} & M_{12} \\ M_{21} & M_{22} \end{pmatrix} \begin{pmatrix} R \\ G \end{pmatrix}$$

$R_{new}$: corrected pixel data of pixel of interest (R component)
$G_{new}$: corrected pixel data of pixel of interest (G component)
$M_{11}$-$M_{22}$: correction matrix coefficient
R: uncorrected pixel data of pixel of interest (R component)
G: uncorrected pixel data of pixel of interest (G component)

S16 in FIG. 2 (Calculation of Angle)

When processing steps S14 (selection of pixel of interest) and S15 (correction of pixel data) have been executed by the correction circuit 220D on all of the pixels in the current frame, the scoring circuit 220E calculates an angle for calculating the degree of inflammation for the pixel data ($R_{new}$,$G_{new}$) for each pixel that was obtained by the correction in processing step S15 (correction of pixel data). Specifically, this processing step S16 is processing for calculating, for each pixel, an angle θ formed by the hemoglobin variation axis AX1 and a line segment L that connects the pixel correspondence point ($R_{new}$,$G_{new}$) and an intersection (reference point) O' of the hemoglobin variation axis AX1 and the mucous membrane variation axis AX2 (see FIG. 3). Note that the reference point O' is located at the coordinates (−150,−75).

S17 in FIG. 2 (Normalization Processing)

When the brightness of the captured image of a body cavity changes according to the degree of illumination with the white light L, the hue of the captured image is influenced by individual differences, the imaged location, the state of inflammation, and the like, but in the RG plane, the hue changes approximately along the hemoglobin variation axis AX1 at an inflamed site with the highest symptom level, and the hue changes approximately along the mucous membrane variation axis AX2 at an inflamed site with the lowest symptom level. It is also inferred that the hue of the captured image at an inflamed site with a moderate symptom level also changes with the same tendency. Specifically, when a pixel correspondence point corresponding to an inflamed site changes according to the degree of illumination with the white light L, a shift occurs in the azimuth angle direction with the reference point O' serving as the origin. In other words, when a pixel correspondence point corresponding to an inflamed site changes according to the degree of illumination with the white light L, the distance from the reference point O' changes while the angle $\theta$ remains constant. This means that the angle $\theta$ is a parameter that is substantially not influenced by change in the brightness of the captured image.

The lower the angle $\theta$ is, the more intense the R component is relative to the G component, which indicates that the symptom level of the inflamed site is higher. Also, the higher the angle $\theta$ is, the more intense the G component is relative to the R component, which indicates that the symptom level of the inflamed site is lower.

In view of this, in this processing step S17, for all of the pixels in the current frame, the scoring circuit 220E normalizes the angle $\theta$ so as to take a value of 255 when the angle $\theta$ is zero and take a value of zero when the angle $\theta$ is $\theta_{MAX}$. Note that $\theta_{MAX}$ is equivalent to the angle formed by the hemoglobin variation axis AX1 and the mucous membrane variation axis AX2. Accordingly, a degree of inflammation that falls within the range of 0 to 255 (8-bit information) is calculated.

S18 in FIG. 2 (Calculation of Inflammation Evaluation Value)

In this processing step S18, the scoring circuit 220E calculates the average value of the degree of inflammation of all of the pixels in the current frame (or calculates an integrated value of the degree of inflammation of all of the pixels) as the overall inflammation evaluation value of the captured image, and generates display data for the calculated inflammation evaluation value (example of display data: Score: OO).

S19 in FIG. 2 (Determination of Display Color in Color Map Image)

In the present embodiment, it is possible to display a color map image obtained by mosaicking a captured image in display colors that correspond to the degree of inflammation. In order to enable the display of a color map image, a table of correspondence between degree of inflammation values and predetermined display colors is stored in a storage region in the scoring circuit 220E. In this table, a display color is associated with each group of 5 values, for example. For example, yellow is associated with the range of degree of inflammation values 0 to 5, different display colors are associated with groups of five higher values according to the color order in the hue circle, and red is associated with the range of values 250 to 255.

In this processing step S19, the display color in the color map image for each pixel in the current frame is determined by the mapping circuit 220F to be, based on the above-described table, the color that corresponds to the value of the degree of inflammation that was obtained in processing step S17 (normalization processing).

S20 in FIG. 2 (Generation of Color Map Image Data)

In this processing step S20, the mapping circuit 220F converts the color data of each pixel in the current frame into data for the display color that was determined in processing step S19 (determination of display color in color map image), and generates color map image data that is made up of pixels to be displayed in the converted display colors.

S21 in FIG. 2 (Overlay Processing)

In this processing step S21, the output circuit 220C sets a coefficient as the ratio for overlaying a normal color image, which is based on normal color image data received from the process circuit 220B, and a color map image, which is based on color map image data generated in processing step S20 (generation of color map image data), and adds the former image data (normal color image data) and the latter image data (color map image data) based on the coefficient.

Note that the setting of the coefficient can be appropriately changed by a user operation. For example, in the case of a desire to display the normal color image more, the coefficient for the color image data is set higher, and in the case of a desire to display the color map image more, the coefficient for the color map image data is set higher.

S22 in FIG. 2 (End Determination)

In this processing step S22, it is determined whether or not the operating mode of the electronic endoscope system 1 has been switched to a mode other than the special mode. If it is determined that the operating mode has not been switched to another mode (S22: NO), the procedure in the special image generation processing in FIG. 2 returns to processing step S11 (input of pixel data of current frame). However, if it is determined that the operating mode has been switched to another mode (S22: YES), the special image generation processing in FIG. 2 ends.

Screen Display Example

The output circuit 220C generates display data for an overlay image including the normal color image and the color map image based on the image data obtained by the addition processing in processing step S21 (overlay processing) in FIG. 2, performs masking processing for masking the peripheral region of the display screen of the monitor 300 (periphery of the image display region), and furthermore generates monitor display screen data in which the inflammation evaluation value is superimposed on the mask region generated by the masking processing. The output circuit 220C converts the generated monitor display screen data into a predetermined video format signal, and outputs the signal to the monitor 300.

Figure 5:
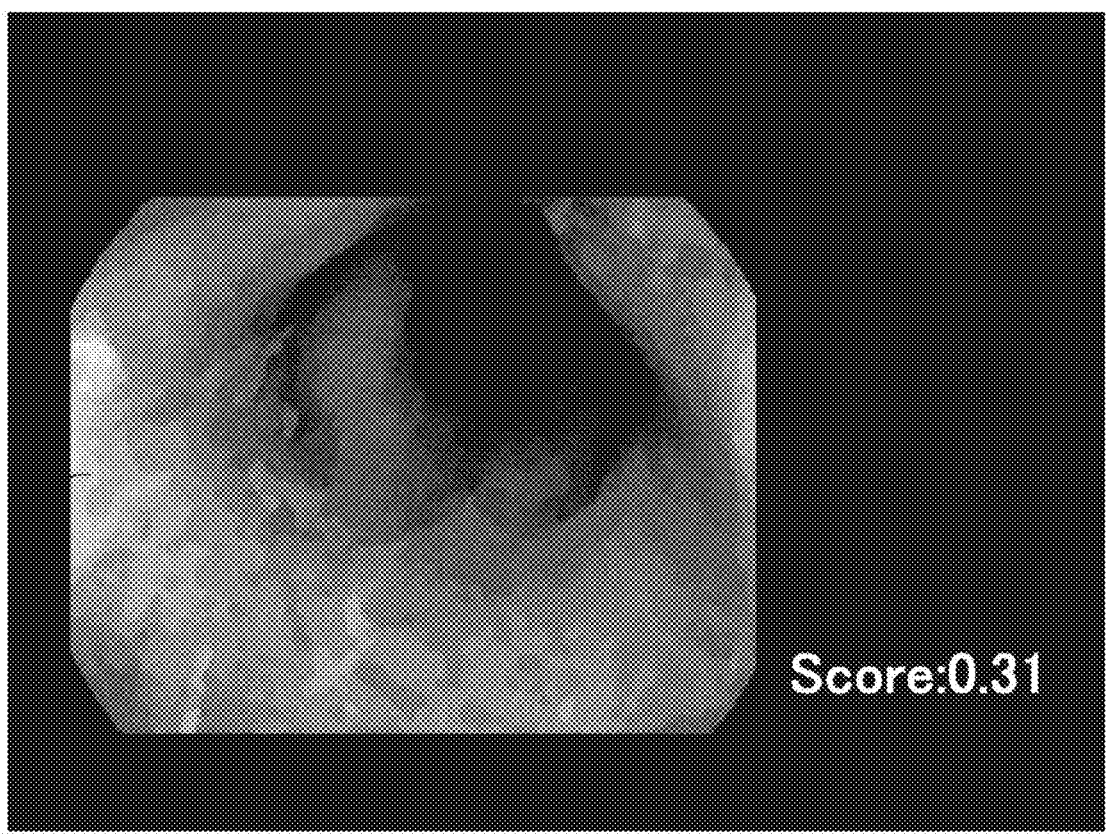
FIG. 5 is a diagram showing an example of a display screen displayed on a monitor display screen in a special mode according to an embodiment of the present invention.

FIG. 5 shows an example of screen display in the special mode. As shown in FIG. 5, the display screen of the monitor 300 includes the intracavitary captured image (overlay image in which the normal image and the color map image are overlaid) in the central region, and a masked screen region surrounding the image display region. The inflammation evaluation value (score) is also displayed in the mask region.

Note that the mode of display of the captured image in the special mode is not limited to being overlay display of a normal color image and a color map image. For example, there are also display modes such as arranging the normal color image and the color map image side-by-side in the same screen, and displaying only the color map image. In the former case, the normal color image and the color map image may both be displayed at the same size, or a configuration is possible in which either the normal color image or the color map image is displayed as the main image, and the other one is displayed as a sub image that is smaller than the main image.

In this way, according to the present embodiment, there is no need to perform complex color space transformation processing, nonlinear calculation processing such as tone enhancement processing, or the like, and an inflammation evaluation value (here, a value correlated with increase/decrease in the hemoglobin pigment of an imaging site) is obtained by merely performing simple calculation processing. In other words, the amount of hardware resources needed for calculation of an inflammation evaluation value is significantly suppressed. Also, the inflammation evaluation value substantially does not vary according to imaging conditions that influence the brightness of the intracavitary captured image (e.g., the degree of illumination with irradiation light), and therefore the operator can make a more objective and accurate diagnosis regarding inflammation.

Operations in Calibration Mode

Figure 6:
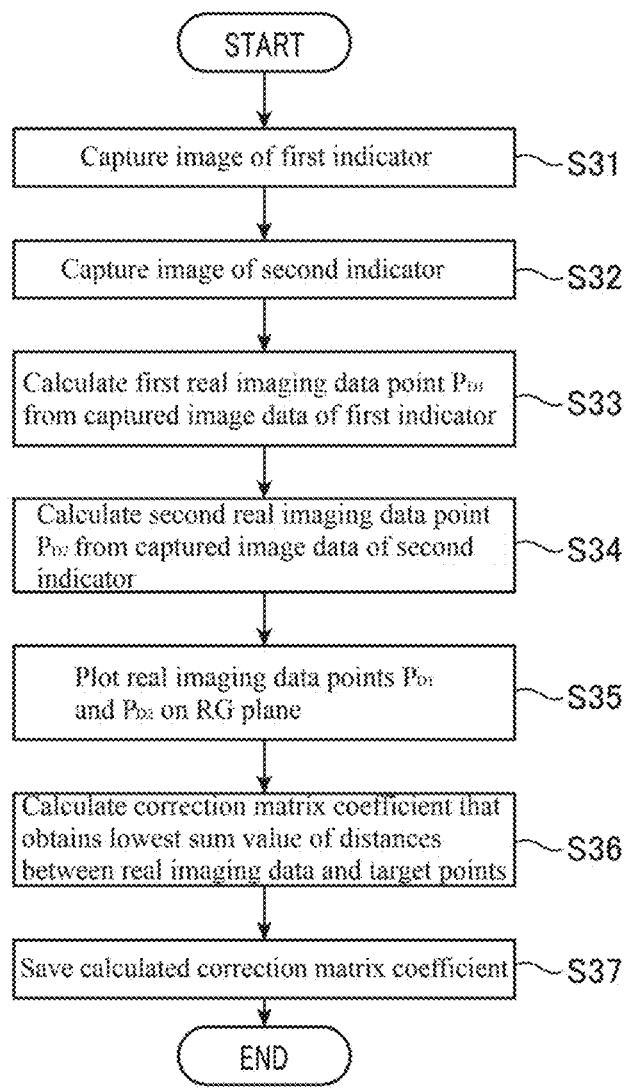
FIG. 6 is a diagram showing a flowchart of calibration processing executed in a calibration mode according to an embodiment of the present invention.
Figure 7:
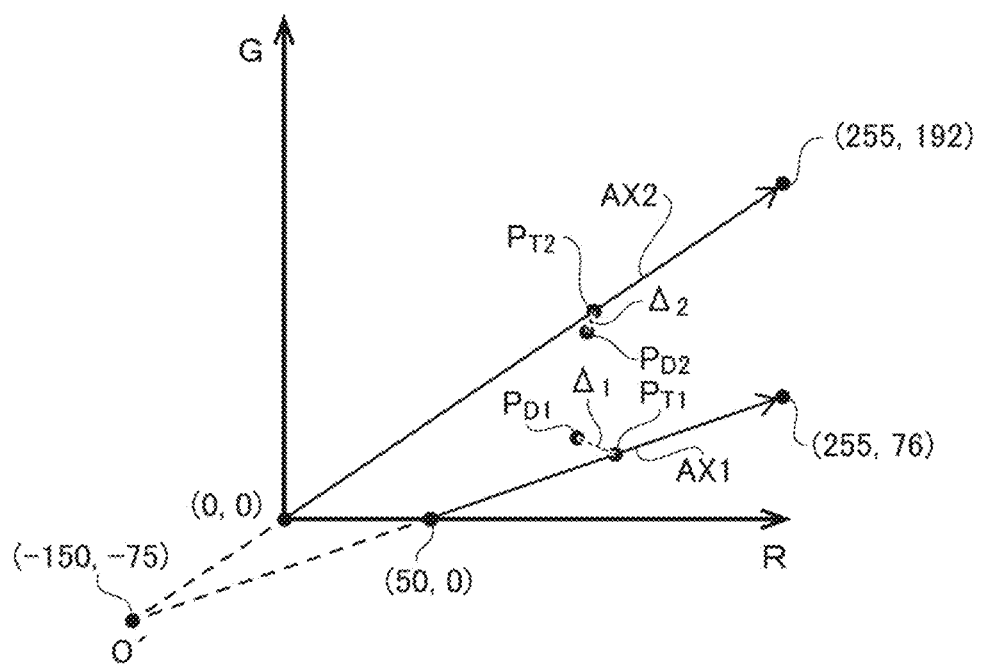
FIG. 7 is a diagram for assisting a description of the calibration processing in FIG. 6.

Next, operations of the electronic endoscope system 1 in the calibration mode will be described. FIG. 6 shows a flowchart of calibration processing executed in the calibration mode. Also, FIG. 7 shows a diagram for assisting the description of the calibration processing in FIG. 6. The calibration processing in FIG. 6 is executed at the time of factory shipment for example, and is started when the operating mode of the electronic endoscope system 1 is switched to the calibration mode.

Note that preparation operations may be performed by a worker prior to the execution of calibration processing. Specifically, the worker adjusts the white balance of the electronic endoscope system 1 with use of a gray card or the like.

When white balance adjustment is complete, the worker sets the electronic endoscope system 1 in a calibration jig and starts calibration software on a terminal (PC) that is connected to the processor 200.

The worker then performs luminance adjustment on a captured image captured by the electronic endoscope 100. For example, the worker manually adjusts the aperture of the diaphragm 212 such that the luminance value of a captured image, which is obtained by imaging a subject for luminance adjustment, coincides with a target luminance value. Note that the luminance value of the captured image can be checked with the calibration software.

When luminance adjustment of the captured image is complete, the worker fixedly arranges a first indicator in the angle of view of the electronic endoscope 100 by setting the first indicator in the calibration jig. Here, the first indicator is an indicator of a first color, which is the color of biological tissue when the symptom level is the highest with respect to a predetermined illness. In the present embodiment, the first indicator is a plate-shaped member colored with a color that corresponds to a predetermined point (later-described first target point $P_{T1}$) on the hemoglobin variation axis AX1 in the RG plane.

S31 in FIG. 6 (Imaging of First Indicator)

In this processing step S31, in accordance with operation input from the worker, the first indicator (surface colored with the first color) is imaged by the electronic endoscope 100, and the resulting captured image data (RAW format, YUV format, or the like) is input to the PC.

S32 in FIG. 6 (Imaging of Second Indicator)

The worker then fixedly arranges a second indicator, in place of the first indicator, in the angle of view of the electronic endoscope 100 by setting the second indicator in the calibration jig. Here, the second indicator is an indicator of a second color, which is the color of biological tissue that is healthy with respect to a predetermined illness. In the present embodiment, the second indicator is a plate-shaped member colored with a color that corresponds to a predetermined point (later-described second target point $P_{T2}$) on the mucous membrane variation axis AX2 in the RG plane.

In this processing step S32, in accordance with operation input from the worker, the second indicator (surface colored with the second color) is imaged by the electronic endoscope 100, and the resulting captured image data (RAW format, YUV format, or the like) is input to the PC. By using the calibration jig, the worker can image the first indicator and the second indicator under the same conditions. Executing processing step S31 (imaging of first indicator) and this processing step S32 acquires captured image data by imaging indicators that are related to a predetermined illness.

S33 in FIG. 6 (Calculation of First Real Imaging Data Point $P_{D1}$)

Execution of this processing step S33 is started in accordance with operation input from the worker or automatically after the capture of a designated number of images (here, two images).

In this processing step S33, the calibration software calculates a first real imaging data point $P_{D1}$ as the real measurement value of the first indicator based on the captured image data for the first indicator that was imaged in processing step S31 (imaging of first indicator). For example, the average value of pixels (e.g., 200×200 pixels) in the central region of the image of the first indicator is calculated as the first real imaging data point $P_{D1}$.

S34 in FIG. 6 (Calculation of Second Real Imaging Data Point $P_{D2}$)

In this processing step S34, the calibration software calculates a second real imaging data point $P_{D2}$ as the real measurement value of the second indicator based on the captured image data for the second indicator that was imaged in processing step S32 (imaging of second indicator). For example, similarly to the first real imaging data point, the average value of pixels (e.g., 200×200 pixels) in the central region of the image of the second indicator is calculated as the second real imaging data point $P_{D2}$.

S35 in FIG. 6 (Plotting of Real Imaging Data on RG Plane)

In this processing step S35, the calibration software plots the first real imaging data point $P_{D1}$ and the second real imaging data point $P_{D2}$ on the RG plane that is associated with a target illness (e.g., gastritis) here as shown in FIG. 7. By execution of this processing step S35, the real imaging data points are plotted in a predetermined color space that is associated with a predetermined illness in accordance with the color components of the real imaging data points.

S36 in FIG. 6 (Calculation of Correction Matrix Coefficient)

As shown in FIG. 7, a first target point $P_{T1}$ that corresponds to the first real imaging data point $P_{D1}$ is set on the hemoglobin variation axis AX1, and a second target point $P_{T2}$ that corresponds to the second real imaging data point $P_{D2}$ is set on the mucous membrane variation axis AX2. The first target point $P_{T1}$ corresponds to the first color of the first indicator, and the second target point $P_{T2}$ corresponds to the second color of the second indicator.

In this processing step S36, the calibration software uses the least squares method or the like to calculate the correction matrix coefficient that obtains the lowest sum value of the distance between the first real imaging data point $P_{D1}$ and the first target point $P_{T1}$ (first distance $\Delta_1$) and the distance between the second real imaging data point $P_{D2}$ and the second target point $P_{T2}$ (second distance $\Delta_2$). Executing this processing step S36 calculates a correction value for correcting the values of the pixels that constitute a captured image captured by an electronic endoscope based on the distances between real imaging data points and predetermined target points in a color space.

Also, the correction matrix coefficient may be calculated using the following expression.

Example of Calculation of Correction Matrix Coefficient $$\begin{pmatrix} M_{11} & M_{12} \\ M_{21} & M_{22} \end{pmatrix} = \begin{pmatrix} REF_{11} & REF_{12} \\ REF_{21} & REF_{22} \end{pmatrix} \begin{pmatrix} MEA_{11} & MEA_{12} \\ MEA_{21} & MEA_{22} \end{pmatrix}^{-1}$$

$M_{11}$-$M_{22}$: correction matrix coefficient
$REF_{11}$, $REF_{21}$: first target point $P_{T1}$
$REF_{12}$, $REF_{22}$: second target point $P_{T2}$
$MEA_{11}$, $MEA_{21}$: first real imaging data point $P_{D1}$
$MEA_{12}$, $MEA_{22}$: second real imaging data point $P_{D2}$ As shown below, the above expression is derived by transforming an expression for correction to correction targets (target points) by applying a correction matrix to measurement values (real imaging data points).

$$\begin{pmatrix} REF_{11} & REF_{12} \\ REF_{21} & REF_{22} \end{pmatrix} = \begin{pmatrix} M_{11} & M_{12} \\ M_{21} & M_{22} \end{pmatrix} \begin{pmatrix} MEA_{11} & MEA_{12} \\ MEA_{21} & MEA_{22} \end{pmatrix}$$

$$\begin{pmatrix} REF_{11} & REF_{12} \\ REF_{21} & REF_{22} \end{pmatrix} \begin{pmatrix} MEA_{11} & MEA_{12} \\ MEA_{21} & MEA_{22} \end{pmatrix}^{-1} =$$

$$\begin{pmatrix} M_{11} & M_{12} \\ M_{21} & M_{22} \end{pmatrix} \begin{pmatrix} MEA_{11} & MEA_{12} \\ MEA_{21} & MEA_{22} \end{pmatrix} \begin{pmatrix} MEA_{11} & MEA_{12} \\ MEA_{21} & MEA_{22} \end{pmatrix}^{-1}$$

$$\begin{pmatrix} REF_{11} & REF_{12} \\ REF_{21} & REF_{22} \end{pmatrix} \begin{pmatrix} MEA_{11} & MEA_{12} \\ MEA_{21} & MEA_{22} \end{pmatrix}^{-1} = \begin{pmatrix} M_{11} & M_{12} \\ M_{21} & M_{22} \end{pmatrix}$$

S37 in FIG. 6 (Saving of Correction Matrix Coefficient)

In this processing step S37, the correction matrix coefficient that was calculated in processing step S36 (calculation of correction matrix coefficient) is saved (stored) in the correction circuit 220D of the processor 200. Accordingly, the calibration processing shown in FIG. 6 is complete.

By executing calibration processing on electronic endoscope systems, values that are approximately the same (values that approach the first target point $P_{T1}$ and the second target point $P_{T2}$ in each electronic endoscope system) are obtained when the first indicator and the second indicator that are associated with a target illness (e.g., gastritis) are imaged by the electronic endoscope systems, and therefore the inflammation evaluation values that are ultimately calculated also take approximately equivalent values. It is therefore understood that it is possible to suppress variation in inflammation evaluation values even when the target illness (e.g., gastritis) is actually imaged by the electronic endoscope systems.

In other words, according to the present embodiment, by limiting the correction target (specifically, setting predetermined colors that are associated with the target illness as the correction targets), it is possible to favorably remove error that remains in the color data that is used when calculating the evaluation value for the target illness (mainly variation caused by individual differences between the optical components of electronic endoscopes 100). Accordingly, the calculation precision of the evaluation value improves.

Also, the electronic endoscope system according to the present embodiment achieves effects and problem solutions such as the following in the applicable technical fields.

First, the electronic endoscope system according to the present embodiment is a diagnostic aid for early discovery of an inflammatory illness.

Second, according to the configuration of the present embodiment, it is possible to display a screen showing the degree of inflammation or enhance the image in a region in which inflammation is occurring, such that the operator can discover mild inflammation that is difficult to view. In particular, mild inflammation is difficult to distinguish from a normal site, and therefore the effects achieved by the configuration of the present embodiment regarding the evaluation of mild inflammation are remarkable.

Third, according to the configuration of the present embodiment, it is possible to provide the operator with an objective evaluation value as an evaluation of the degree of inflammation, thus making it possible to reduce differences in diagnoses among operators. In particular, there is a large advantage of being able to provide an operator having little experience with an objective evaluation value obtained by the configuration of the present embodiment.

Fourth, according to the configuration of the present embodiment, the load of image processing is reduced, thus making it possible to perform real-time display of images of an inflamed site. This makes it possible to improve diagnosis precision.

Fifth, according to the configuration of the present embodiment, the processing load of evaluation value calculation is reduced, thus making it possible to display a color map image (image showing the degree of inflammation) and a normal image side-by-side or in a composited manner without lag. For this reason, it is possible to display a color map image without extending the inspection time, thus making it possible to avoid an increase in the burden on the patient.

The site that is to be observed in the present embodiment is a respiratory organ or the like, or a digestive organ or the like, for example. Here, "respiratory organ or the like" includes the lungs, the ears, the nose, and the throat, for example. "Digestive organ or the like" includes the large intestine, the small intestine, the stomach, the duodenum, and the uterus, for example. The electronic endoscope system according to the present embodiment is thought to have even more remarkable effects when the observation target is the large intestine. The following are specific reasons for this.

The large intestine is susceptible to diseases that can be evaluated using inflammation as a reference, and the advantage of discovering inflamed sites is greater than in the case of other organs. In particular, the inflammation evaluation value obtained by the present embodiment is effective as an indicator of inflammatory bowel disease (IBD), which is typified by ulcerative colitis. A method of treatment has not been established for ulcerative colitis, and therefore using the electronic endoscope system having the configuration of the present embodiment is very effective in making an early diagnosis and suppressing the progression of the illness.

The large intestine is a narrower and longer organ than the stomach and the like, and the obtained images have greater depth and are darker as the depth increases. According to the configuration of the present embodiment, it is possible to suppress variation in the evaluation value caused by changes in the brightness in the image. Accordingly, when the electronic endoscope system according to the present embodiment is applied to the observation of the large intestine, the effects of the present embodiment are remarkable. In other words, the electronic endoscope system according to the present embodiment is preferably a respiratory organ electronic endoscope system or a digestive organ electronic endoscope system, and is more preferably a large intestine electronic endoscope system.

Also, although mild inflammation is generally difficult to diagnose, according to the configuration of the present embodiment, by displaying the results of degree of inflammation evaluation on the screen for example, it is possible to avoid a situation in which the operator misses mild inflammation. In particular, in the case of mild inflammation, the determination criteria are not clear, and this is a factor that causes a large amount of individual differences between operators. In this regard as well, according to the configuration of the present embodiment, it is possible to provide the operator with an objective evaluation value, thus making it possible to reduce variation in diagnoses caused by individual differences.

Note that the above-described configuration of the present embodiment is applicable to the calculation of an evaluation value of not only the degree of inflammation, but also cancer, polyps, and various other lesions that are accompanied by a color change, and advantageous effects similar to those described above can be achieved in these other cases as well. In other words, the evaluation value of the present embodiment is preferably an evaluation value for a lesion that is accompanied by a color change, and includes an evaluation value of at least any of inflammation, cancer, and polyps.

An illustrative embodiment of the present invention has been described above. The embodiments of the present invention are not limited to the embodiment described above, and various changes can be made without departing from the scope of the technical idea of the present invention. For example, appropriate combinations of embodiments and the like explicitly given as examples in this specification and obvious embodiments and the like are also encompassed in embodiments of the present invention.

In the above embodiment, a worker selects an indicator that has a first color (color of biological tissue when the symptom level is the highest with respect to a predetermined illness) as the first indicator, and selects an indicator that has a second color (color of biological tissue when healthy with respect to a predetermined illness) as the second indicator. For this reason, in the above embodiment, calibration is performed with higher precision the closer the colors are to the first color and the second color (i.e., correction targets) in the color space. In other words, calibration precision is lower the farther the colors are from the correction targets in the color space (e.g., a color that is improbable with inflammation, such as light blue).

Accordingly, it is sufficient that the worker selects, as an indicator to be set in the calibration jig, an indicator that corresponds to the symptom level that is to be scored with particularly high precision using the electronic endoscope system 1. For example, in the case of a desire to score mild inflammation with high precision, the operator need only select, as the first indicator, an indicator of the color of biological tissue when mild inflammation has occurred.

Note that the more subdivided the provided indicators are, the more difficult it is for the operator to select an appropriate indicator. In view of this, the system controller 202 can perform control such that when an operation for designating a symptom level is received from the worker via a connected peripheral device (e.g., a keyboard), the indicator that corresponds to the designated symptom level is displayed on the display screen of the monitor 300 or notified by audio playback (i.e., the user is informed of the indicator). Accordingly, the operator can accurately select an appropriate indicator from among multiple indicators.

Also, in the above embodiment, the inflammation evaluation value is calculated using the R component and the G component (RG two-dimensional color space) of each pixel, but in another embodiment, in place of the RG two-dimensional color space, it is possible to use the RB two-dimensional color space or a three-dimensional color space such as HSI, HSV, or Lab to calculate an evaluation value related to a target illness that corresponds to the color space and is different from the above embodiment (e.g., stomach atrophy or a large intestinal tumor). In this case, the correction matrix coefficient is calculated using indicators and target points that are different from the above embodiment.

Multiple types of correction matrix coefficients that correspond to various types of target illnesses may be saved in the correction circuit 220D of the processor 200. By switching the correction matrix coefficient according to the illness that is to be diagnosed, it is possible to perform evaluation value calculation that is stable (has little variation due to individual differences) for the corresponding target illness.

The invention claimed is:

1. A correction data generation method executed by a computer, the method comprising:
    acquiring captured image data by imaging an indicator that is related to a predetermined illness, wherein first captured image data is acquired by imaging a first indicator of a first color that is a color of biological tissue when a symptom level is a predetermined first level with respect to the predetermined illness, and second captured image data is acquired by imaging a second indicator of a second color that is a color of biological tissue when a symptom level is a predetermined second level with respect to the predetermined illness;
    plotting a real imaging data point that corresponds to the acquired captured image data in a predetermined color space that is associated with the predetermined illness in accordance with a color component of the data point, wherein first and second data points that correspond to the acquired first and second captured image data are plotted in the color space in accordance with color components of the first and second data points;
    calculating a correction value for correcting values of pixels that make up a captured image captured by an electronic endoscope based on a distance between the data point and a predetermined target point in the color space, wherein the correction value is calculated based on a distance between the first data point and a predetermined first target point in the color space and a distance between the second data point and a predetermined second target point in the color space; and
    storing the calculated correction value.

2. The correction data generation method according to claim 1, further comprising:
    accepting an operation designating a symptom level from a user; and
    informing the user of an indicator that corresponds to the accepted symptom level.

3. The correction data generation method according to claim 1, wherein in the calculating, a matrix coefficient that obtains a lowest sum value of the distance between the first data point and the first target point and the distance between the second data point and the second target point is calculated as the correction value.

4. The correction data generation method according to claim 1, wherein the color space is a two-dimensional color space that includes an R component axis and a G component axis that is orthogonal to the R component axis.

5. The correction data generation method according to claim 2,
wherein the first color is a color of biological tissue when the symptom level is highest with respect to the predetermined illness, and
wherein the first target point is a point located on an axis highly correlated with hemoglobin pigment in the color space.

6. The correction data generation method according to claim 2,
wherein the second color is a color of biological tissue that is healthy with respect to the predetermined illness, and
wherein the second target point is a point located on an axis highly correlated with a hue of a mucous membrane in a body cavity in the color space.

7. A correction data generation apparatus comprising:
an acquirer which acquires captured image data by imaging an indicator that is related to a predetermined illness, wherein first captured image data is acquired by imaging a first indicator of a first color that is a color of biological tissue when a symptom level is a predetermined first level with respect to the predetermined illness, and second captured image data is acquired by imaging a second indicator of a second color that is a color of biological tissue when a symptom level is a predetermined second level with respect to the predetermined illness;
a plotter which plots a real imaging data point that corresponds to the acquired captured image data in a predetermined color space that is associated with the predetermined illness in accordance with a color component of the data point, wherein first and second data points are plotted, the first and second data points correspond to the acquired first and second captured image data in the color space in accordance with color components of the first and second data points;
a calculator which calculates a correction value for correcting values of pixels that make up a captured image captured by an electronic endoscope based on a distance between the data point and a predetermined target point in the color space, wherein the correction value is calculated based on a distance between the first data point and a predetermined first target point in the color space and a distance between the second data point and a predetermined second target point in the color space; and
a storage which stores the calculated correction value.

8. The correction data generation apparatus according to claim 7, further comprising:
an acceptor which accepts an operation designating a symptom level from a user; and
an informer which informs the user of an indicator that corresponds to the accepted symptom level.

9. The correction data generation apparatus according to claim 7, wherein the calculator calculates, as the correction value, a matrix coefficient that obtains a lowest sum value of the distance between the first data point and the first target point and the distance between the second data point and the second target point.

10. The correction data generation apparatus according to claim 7, wherein the color space is a two-dimensional color space that includes an R component axis and a G component axis that is orthogonal to the R component axis.

11. The correction data generation apparatus according to claim 8, wherein the first target point is a point located on an axis highly correlated with hemoglobin pigment in the color space.

12. The correction data generation apparatus according to claim 8, wherein the second target point is a point located on an axis highly correlated with a hue of a mucous membrane in a body cavity in the color space.

13. The correction data generation method according to claim 1, wherein the predetermined first target point corresponds to the first color of the first indicator and the predetermined second target point corresponds to the second color of the second indicator.

14. The correction data generation apparatus according to claim 7, wherein the predetermined first target point corresponds to the first color of the first indicator and the predetermined second target point corresponds to the second color of the second indicator.

* * * * *